United States Patent [19]

Penco et al.

[11] 4,251,513

[45] Feb. 17, 1981

[54] 9-DESACETYL-9-ETHYLEN OXIDE DAUNORUBICIN, PROCESS FOR ITS MANUFACTURE AND USE THEREFOR

[75] Inventors: Sergio Penco; Francesco Angelucci; Federico Arcamone, all of Milan, Italy

[73] Assignee: Farmitalia Carlo Erba S.p.A., Milan, Italy

[21] Appl. No.: 877,754

[22] Filed: Feb. 14, 1978

[30] Foreign Application Priority Data

Feb. 22, 1977 [GB] United Kingdom ............... 7331/77

[51] Int. Cl.$^2$ .................... A61K 31/70; C07H 15/24

[52] U.S. Cl. ................... 424/180; 536/17 A; 424/181

[58] Field of Search .................. 536/17, 17 A, 4; 424/180

[56] References Cited

U.S. PATENT DOCUMENTS

| | | | |
|---|---|---|---|
| 3,803,124 | 4/1974 | Arcamone et al. | 536/17 A |
| 4,078,138 | 3/1978 | Akita et al. | 536/17 |

Primary Examiner—Johnnie R. Brown
Attorney, Agent, or Firm—Hubbell, Cohen, Stiefel & Gross

[57] ABSTRACT

9-Desacetyl-9-ethylen oxide daunorubicin hydrochloride is an effective antitumor antibiotic.

5 Claims, No Drawings

9-DESACETYL-9-ETHYLEN OXIDE DAUNORUBICIN, PROCESS FOR ITS MANUFACTURE AND USE THEREFOR

BACKGROUND OF THE INVENTION

The invention described herein was made in the course of work under a grant from the U.S. Department of Health, Education and Welfare. The invention relates to a new antitumor compound which is a derivative of the known compound daunorubicin.

CROSS REFERENCE TO RELATED APPLICATIONS

This application is related to and incorporates by reference the contents of copending application Ser. No. 860,448 filed Dec. 14, 1977, abandoned.

SUMMARY OF THE INVENTION

The present invention provides, in one aspect thereof a new antitumor antibiotic of the formula:

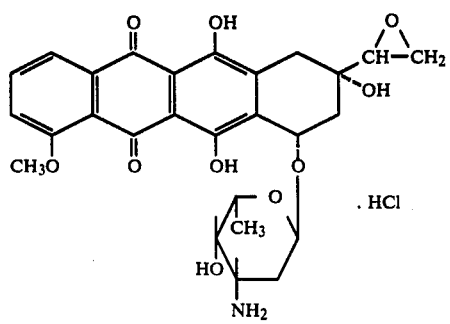

In another aspect the invention provides a novel method for preparing the compound of formula (I). According to the method, (I) is synthesized, starting from 9-desacetyl-9-formyl-N-trifluoroacetyl daunorubicin of formula (II). Compound II is described in the above-identified copending application which corresponds to British Patent Application No. 53455/76. The treatment of the compound of formula (II) in methanol with excess diazomethane gives the epoxide derivative of formula (I) in good yield. The choice of the solvent to be used is of critical importance in obtaining the epoxide derivative. In fact, if the reaction is carried out in an aprotic solvent such as methylene chloride or chloroform, the yield of the epoxide derivative is very low because of the simultaneous formation of the corresponding methyl ketone derivative. The reaction is carried out at room temperature for 3 hours; the other operating conditions are not critical.

The scheme of the reaction is as follows:

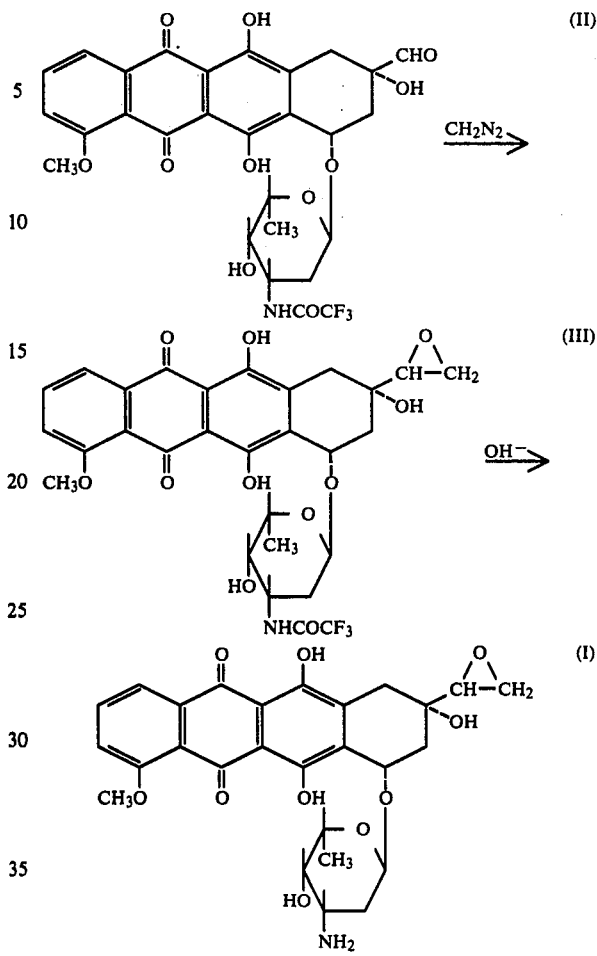

More particularly, a methanolic solution of the compound of formula (II), at a temperature of 20° C., is treated with an excess of an ethereal solution of $CH_2N_2$. The diazomethane must be added in several portions in order to avoid etherification of the phenolic hydroxy groups. The crude compound (III), obtained by evaporation of the solvents under vacuum, before the removal of the N-trifluoroacetyl group, can be purified by chromatography on a column of silicic acid using chloroform:acetone in a ratio 9:1 (by vol.) as the eluent. The hydrolysis of the protective group is performed using a dilute aqueous alkali as exemplified below.

Finally, in another aspect, the invention provides a method of treating certain mammalian tumors using the compound of the invention as described in more detail below.

DESCRIPTION OF THE PREFERRED EMBODIMENTS

The following non-limitative examples are given in order to describe in more detail the process for the preparation of the compound of the invention.

EXAMPLE 1

9-Desacetyl-ethylen oxide-N-trifluoroacetyldaunorubicin (III)

A solution of 1 g. of 9-desacetyl-9-formyl-N-trifluoroacetyldaunorubicin in 150 ml. of anhyrous methanol was treated, while stirring at room temperature, with 60 ml. of an ethereal solution of diazomethane (prepared from 20 g. of N-nitrosomethylurea), added in six 10 ml. portions over a period of three hours. The reaction mixture was then evaporated under vacuum to dryness. The resulting solid residue was chromatographed on a column of silicic acid using a mixture of chloroform:acetone (9:1, v/v) as the eluting agent, thereby giving 0.35 g. of pure 9-desacetyl-9-ethylen oxide-N-trifluoroacetyldaunorubicin. TLC on Merck Kieselgel HF plates using the solvent system chloroform:acetone (2:1, v/v): Rf=0.57.

EXAMPLE 2

9-Desacetyl-9-ethylen oxide-daunorubicin hydrochloride (I)

9-Desacetyl-9-ethylen oxide-N-trifluoroacetyldaunorubicin (0.2 g.) was dissolved in 20 ml. of 0.1 N aqueous sodium hydroxide. The resulting solution, after standing for 30 minutes at 0° C., was treated with 0.1 N aqueous hydrogen chloride to adjust the pH to 8.6 and was then extracted repeatedly with chloroform. The combined chloroform extracts, after being dried over $Na_2SO_4$, were concentrated to a small volume (20 ml.). Upon addition of the stoichiometric amount of 0.1 N methanolic hydrogen chloride and excess ether to the solution, a red precipitate was obtained. The precipitate was collected, washed with ether and dried under vacuum.

M.P. 195° C. (dec.) TLC on Merck Kieselgel HF plates using a mixture of chloroform:methanol:water (13:6:1 v/v) as a solvent: Rf=0.65.

PMR (CDCl$_3$): 1.35δ (d, ζ 6.5 H$_Z$, CH$_3$—C(H)); 4.03δ (s, CH$_3$O); 5.25δ (broad s, W$_H$ 6.5 H$_Z$, C-7-H); 5.47δ (broad s, W$_H$ 5.5 H$_Z$, C-1'-H); 7.2–8.2δ (m, 3 aromatic protons).

Biological Activity

9-Desacetyl-9-ethylen oxide daunorubicin hydrochloride was tested under the auspices of NCI—National Institute of Health, Bethesda, Md., USA, against Lymphocytic Leukemia P$_{388}$ according to the procedure described in Cancer Chemotherapy Reports, Part 3, Vol. 3, page 9 (1972).

The data in the following Table illustrates the antitumor activity of this compound.

The compound of the invention was compared with daunorubicin by treating CDF, female mice infected with tumor cells: the i.p. injections were made on days 5, 9 and 13 with a 4 day interval between each single injection starting from the fifth day after tumor transplantation in mice.

TABLE

| Compound | Schedule of Treatment in Days (i.p.) | Dose mg./kg. | T/C % |
|---|---|---|---|
| 9-Desacetyl-9-ethylen oxide-daunorubicin . HCl | 5,9,13 | 50 | 120 |
|  |  | 25 | 118 |
|  |  | 12.5 | 113 |
|  |  | 6.25 | 113 |
|  |  | 3.13 | 93 |
| Daunorubinin . HCl | 5,9,13 | 32 | 104 |
|  |  | 16 | 127 |
|  |  | 8 | 132 |
|  |  | 4 | 123 |
|  |  | 2 | 118 |

Variations and modifications can, of course, be made without departing from the spirit and scope of the invention.

Having thus described our invention, what we desire to secure by Letters Patent and hereby claim is:

1. The compound having the formula:

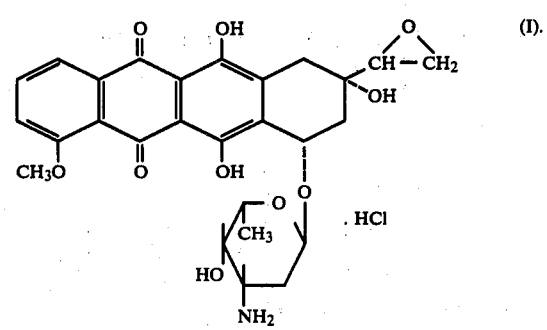

2. A process for preparing the compound according to claim 1, comprising reacting 9-desacetyl-9-formyl-N-trifluoroacetyl daunorubicin dissolved in anhydrous methanol with excess diazomethane to form 9-desacetyl-9-ethylen oxide-N-trifluoroacetyl daunorubicin, subjecting the latter to mild alkaline hydrolysis to remove the N-trifluoroacetyl protecting group and isolating the desired 9-desacetyl-9-ethylen oxide daunorubicin as the hydrochloride.

3. A process according to claim 2, wherein the diazomethane is dissolved in ether and the reaction is effected at room temperature.

4. A process according to claim 2, wherein the mild alkaline hydrolysis is effected with 0.1 N NaOH at about 0° C. for about 30 minutes.

5. A method of treating a host afflicted with transplanted lymphocytic leukemia P$_{388}$ which comprises intraperitoneally administering to a host afflicted therewith, a therapeutically effective amount of the compound according to claim 1.

* * * * *

UNITED STATES PATENT AND TRADEMARK OFFICE
CERTIFICATE OF CORRECTION

PATENT NO. : 4,251,513

DATED : February 17, 1981

INVENTOR(S) : Sergio Penco, et al.

It is certified that error appears in the above—identified patent and that said Letters Patent is hereby corrected as shown below:

```
Title page:       "Ethylen"  should read -- Ethylene --.
Column 1, line 1: "Ethylen"  should read -- Ethylene --.
Column 2, line 64: "9-Desacetyl-ethylen" should read
                   -- 9-Desacetyl-9-ethylene --.
Column 3, line 9:  "ethylen" should read -- ethylene --.
Column 3, line 16: "ethylen" should read -- ethylene --.
Column 3, line 18: "ethylen" should read -- ethylene --.
Column 3, line 41: "ethylen" should read -- ethylene --.
Column 4, line 6:  "ethylen" should read -- ethylene --.
Column 4, line 39: "ethylen" should read -- ethylene --.
Column 4, line 42: "ethylen" should read -- ethylene --.
```

Signed and Sealed this

Fourth Day of August 1981

[SEAL]

Attest:

GERALD J. MOSSINGHOFF

Attesting Officer        Commissioner of Patents and Trademarks